(12) United States Patent
Hauck et al.

(10) Patent No.: US 8,032,306 B2
(45) Date of Patent: Oct. 4, 2011

(54) COMPUTERIZED SYSTEM AND METHOD FOR DOCUMENTING PATIENT VITAL SIGNS DURING BLOOD PRODUCT ADMINISTRATION AND TRANSFUSION

(75) Inventors: Arthur J. Hauck, Kansas City, MO (US); Lori N. Cross, Kansas City, MO (US); Jeffrey D. Fry, Lansing, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 1092 days.

(21) Appl. No.: 11/025,096

(22) Filed: Dec. 29, 2004

(65) Prior Publication Data

US 2006/0149588 A1 Jul. 6, 2006

(51) Int. Cl.
  *G06F 19/00* (2011.01)
  *G01N 33/48* (2006.01)
  *A61M 5/00* (2006.01)
  *G06Q 10/00* (2006.01)
  *G06Q 50/00* (2006.01)

(52) U.S. Cl. .............. 702/19; 356/39; 604/7; 705/2; 705/3; 707/769

(58) Field of Classification Search .............. None
See application file for complete search history.

(56) References Cited

U.S. PATENT DOCUMENTS

| | | | |
|---|---|---|---|
| 6,454,708 B1 * | 9/2002 | Ferguson et al. | 600/300 |
| 6,983,884 B2 * | 1/2006 | Auchinleck | 235/385 |
| 7,490,766 B2 | 2/2009 | Auchinleck | |
| 7,490,767 B2 | 2/2009 | Auchinleck | |
| 2002/0147390 A1 * | 10/2002 | Markis et al. | 600/301 |
| 2009/0121009 A1 | 5/2009 | Auchinleck | |
| 2009/0231124 A1 * | 9/2009 | Klabunde et al. | 340/539.12 |

OTHER PUBLICATIONS

Brodheim (Symposium on Computers in the Clinical Laboratory from Clinics in Laboratory Medicine (1983) vol. 3, No. 1, pp. 111-132).*
AuBuchon JP, Kruskall MS, "Transfusion safety: realigning efforts with risks." Transfusion 1997:37, 1211-1216.
Baele PL, DeBruyere M, Deneys V, Dupont E, Flament J, Lambermont M, et al. "Bedside Transfusion Errors." A Prospective Survey by the Belgium SAnGUIS Group. Vox Sang 1994;66:117-121.
The Health Industry Bar Code (HIBC) Provider Applications Standard, ANSI/HIBC Jan. 1996. American National Standards Institute, Inc. 1996.
Office Action mailed Oct. 19, 2007 for U.S. Appl. No. 11/018,660.
Office Action mailed Jun. 23, 2008 for U.S. Appl. No. 11/108,660.
Office Action mailed Jan. 6, 2009 for U.S. Appl. No. 11/018,660.
Office Action mailed Nov. 20, 2009 for U.S. Appl. No. 11/018,160.
Non-Final Office Action dated Apr. 14, 2010 for U.S. Appl. No. 11/018,160.
Non-Final Office Action dated Sep. 14, 2010 for U.S. Appl. No. 11/018,160.

* cited by examiner

*Primary Examiner* — Lori A Clow
(74) *Attorney, Agent, or Firm* — Shook, Hardy & Bacon L.L.P.

(57) ABSTRACT

A computerized system and method for processing patient vital signs during blood product administration in a computerized healthcare environment is provided. A blood product to be administered to a patient is identified. The patient is identified. Vital signs for the patient are received during blood product administration by a healthcare provider and automatically, without user intervention, the vital signs for the patient are documented in a database.

19 Claims, 7 Drawing Sheets

| PRODUCT ID | TYPE | PATIENT | COMPATIBLE? | DATE COMP. TEST | TEST VALID FOR | DISPENSED? | TIME DISPENSED | HOW LONG TO TRANSFUSE? | COMPLETED? |
|---|---|---|---|---|---|---|---|---|---|
| 001 | AB- | A | YES | 5/10/05 8:00 | 72 HRS | YES | | 5/11/05 1:30 | |
| 001 | AB- | B | NO | 5/10/05 9:00 | 72 HRS | NO | | | |
| 002 | O+ | C | YES | 5/10/05 10:00 | 72 HRS | YES | 11:00 | 5/11/05 1:30 | YES |
| 002 | O+ | D | NO | 5/10/05 22:00 | 72 HRS | NO | | | |
| 003 | AB- | A | YES | 5/10/05 8:00 | 72 HRS | NO | | | |
| 003 | AB- | C | NO | 5/10/05 10:00 | 72 HRS | | | | |

FIG. 4.

COMPUTERIZED SYSTEM AND METHOD FOR DOCUMENTING PATIENT VITAL SIGNS DURING BLOOD PRODUCT ADMINISTRATION AND TRANSFUSION

CROSS-REFERENCE TO RELATED APPLICATIONS

This application is related by subject matter to the inventions disclosed in the commonly assigned U.S. patent application Ser. No. 11/018,660, entitled "COMPUTERIZED SYSTEM AND METHOD FOR SAFELY TRANSFUSING BLOOD PRODUCTS," filed on Dec. 21, 2004, now allowed and U.S. patent application Ser. No. 11/018,160, entitled "SYSTEM AND METHOD FOR AUTOMATICALLY NOTIFYING A BLOOD BANK DATABASE OF BLOOD PRODUCT ADMINISTRATION AND TRANSFUSION," filed Dec. 21, 2004, now abandoned.

STATEMENT REGARDING FEDERALLY SPONSORED RESEARCH OR DEVELOPMENT

Not applicable.

FIELD OF THE INVENTION

The present invention relates generally to the field of computer software. More particularly, the invention relates to a system and method for documenting patient vital signs during blood product administration.

BACKGROUND

In the United States today, transfusion of incompatible blood is the most common cause of serious morbidity and mortality related to transfusion. Transfusion to unintended recipients has been reported to occur at a rate as high as 1 in 400 units and each of these events has the potential for causing one of the approximately two dozen fatal transfusion reactions reported annually.

Errors associated with administration of incompatible blood in fatal transfusion reactions include misidentification of patient samples, errors within the laboratory and misidentification of recipients at the time of transfusion.

Current manual mechanisms for patient identification at the time of blood product transfusion require a healthcare provider to assess and compare the patient identification information of the actual patient and the blood product dispensed for transfusion purposes. Manual mechanisms have inherent flaws, such as failure of personnel to follow established policies and procedures which may allow the personnel to bypass the manual identification checks. Other flaws include failure of personnel to accurately compare the intended recipient to the actual recipient and failure of personnel to accurately compare the intended blood product to the actual blood product to be transfused.

Traditionally, patient identification has relied on manual comparison of one or more identifiers such as name, medical record number or financial number on a transfusion request form with information on a patient wrist band. In addition, many transfusion services have utilized secondary labeling systems (such as Hollister, Typenex, Secureline) to identify patients from whom samples have been drawn for compatibility testing and for matching products to patients at the time of blood administration.

Current automated systems for patient identification at the time of blood product transfusion are flawed in a number of respects. For instance, these systems do not provide real-time access to the direct blood product inventory information from the blood bank department nor do they provide real-time access to blood product testing results from the blood bank department, including compatibility testing results.

Current manual mechanisms for blood transfusion patient assessment and vital sign documentation also have a number of inherent flaws, such as failure to document all appropriate observations and activities, and inaccurate entry of data. Furthermore, manual mechanisms for blood transfusion patient assessment and vital sign documentation are time-consuming and costly.

Current automated systems for blood transfusion patient assessment and vital sign documentation also have a number of flaws. These systems cannot capture data related to the blood product transfusion, patient vital signs and assessment. This is due to the disintegration of the processes for blood product testing, release for transfusion and inventory (and product) documentation done by the blood bank department, and the processes typically performed by the nursing department for the actual transfusion documentation, including patient assessment, vital signs processing, and transfusion activities.

Accordingly, it would be beneficial if there was an automated system and method to eliminate transfusion of blood to unintended recipients. It would be beneficial if the blood product identity is maintained throughout processing in the laboratory and that the compatibility testing results for the blood product recipient be confirmed before blood products are infused. It would further be beneficial to capture and document patient vital signs during blood transfusion. It would also be beneficial to be able to automatically update the blood bank database when a blood product has been administered. Finally, it would be beneficial to integrate the processes performed by the blood bank department and the clinicians at the point of care.

SUMMARY

In one embodiment of the present invention, a method for processing patient information during blood product administration in a computerized healthcare environment is provided. Patient vital signs during blood product administration are received. It is determined whether the patient vital signs are within an acceptable range. Whether the patient vital signs are within an acceptable range is automatically documented in the patient's electronic medical record.

In another embodiment of the present invention, a method for processing patient vital signs during blood product administration in a computerized healthcare environment is provided. A blood product to be administered to a patient is identified. The patient is identified. Vital signs for the patient are received during blood product administration by a healthcare provider and automatically, without user intervention, the vital signs for the patient are documented in a database.

In yet another embodiment, a computerized system for processing patient vital signs during blood product administration is provided. The system comprises a first identifying component for identifying a blood product to be administered to a patient and a second identifying component for identifying the patient. The system further comprises a receiving component for receiving vital signs for the patient during blood product administration by a healthcare provider and a documenting component for automatically, without user intervention, documenting the vital signs for the patient in a database.

BRIEF DESCRIPTION OF THE SEVERAL VIEWS OF THE DRAWINGS

The present invention is described in detail below with reference to the attached drawing figures, wherein:

FIG. 4 is an exemplary table of information regarding blood product units to be used in accordance with an embodiment of the present invention;

DETAILED DESCRIPTION OF THE INVENTION

One embodiment of the present invention integrates in a closed loop the blood product administration and transfusion processes by verifying patient identity, patient/product compatibility, and product dispense status against a database. The validation may occur at the patient bedside before the start of transfusion. In another embodiment of the present invention, during the blood transfusion, patient vital signs are documented and should a reaction occur, the details of the reaction are recorded and a reaction investigation initiated. In yet another embodiment of the present invention, at the conclusion of the blood transfusion, the volume of product infused is recorded and the status of the product may be updated to transfuse in the blood bank database.

The embodiments of the present invention provide a unique solution to seamlessly unify the various blood transfusion practices across different departments and patient care areas operating within a single organization or across organizations. Patient identification prior to the initiation of a blood product transfusion is provided, helping to ensure that patients are not transfused inappropriately. The ability to interactively document transfusion activities and patient assessment information is also provided. Information that can be defaulted or derived can be automatically entered or displayed, thus eliminating opportunities for human error. The blood bank department is notified automatically as to the real-time status of the actual blood product unit, thus ensuring accurate, real-time blood product inventory information.

Figure 1:
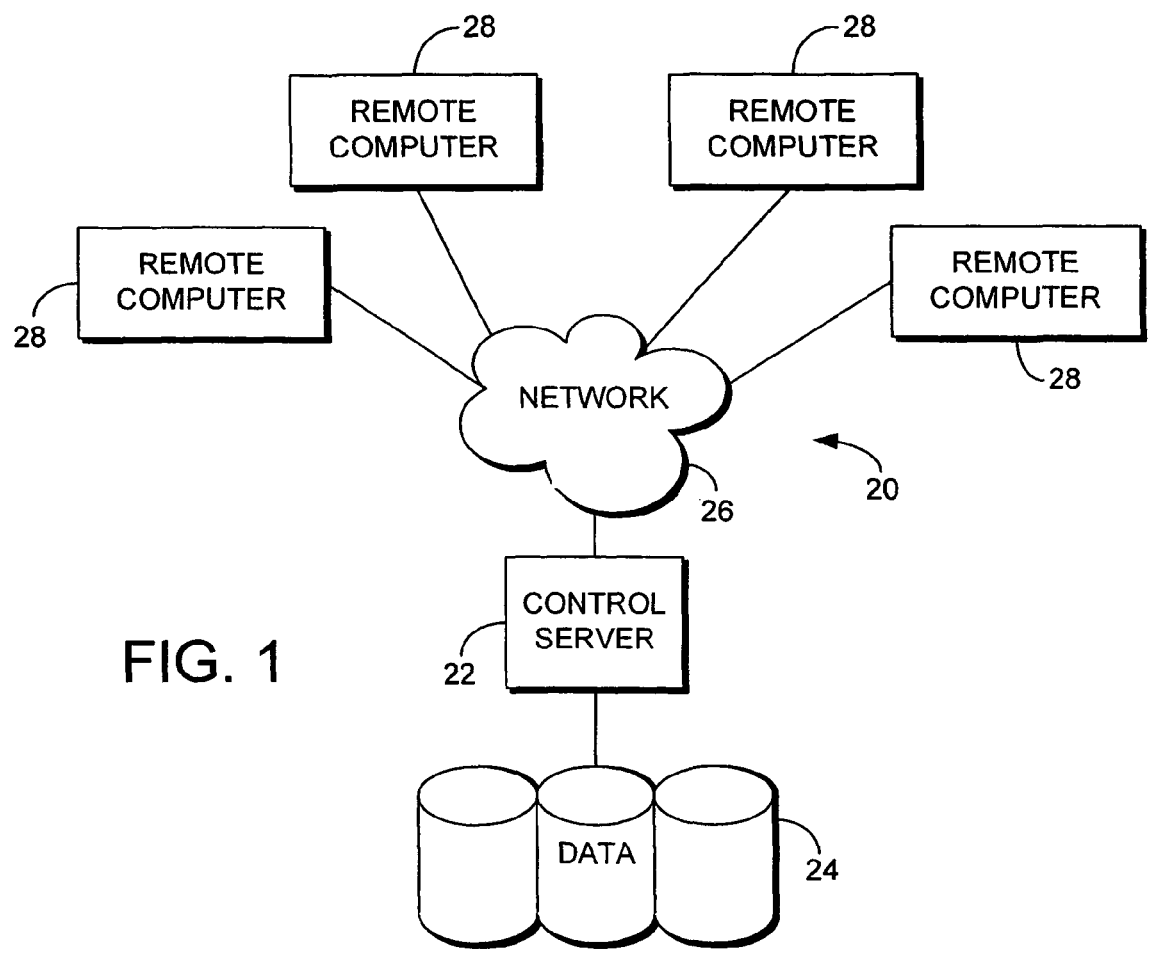
FIG. 1 is a block diagram of a computing system environment suitable for use in implementing the present invention.

With reference to FIG. 1, an exemplary medical information system for implementing the invention includes a general purpose computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, hospital administration, veterinary environment and home healthcare environment. Clinicians include, but are not limited to, the treating physician, specialists such as surgeons, radiologists and cardiologists, emergency medical technicians, physician's assistants, nurse practitioners, nurses, nurse's aides, microbiologists, laboratory experts, researchers, veterinarians, students and the like. The remote computers may also be physically located in non-traditional medical care environments so that the entire healthcare community is capable of integration on the network. Remote computers 28 may be a personal computer, server, router, a network PC, a peer device, other common network node healthcare device or the like, and may include some or all of the elements described above relative to server 22. The devices can be personal digital assistants or other like devices. Computer network 26 may be a local area network (LAN) and/or a wide area network (WAN), but may also include other networks including Internet networks via wired or wireless capability. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. By way of example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Commands and information may also be sent directly from a remote healthcare device to the server 22. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Although the method and system are described as being implemented in a WINDOWS operating system, operating in conjunction with an Internet-based system, one skilled in the art would recognize that the method and system can be implemented in any system supporting the processing of blood products and patient information. As contemplated by the language above, the method and system of the present invention may also be implemented on a stand-alone desktop, personal computer, or any other computing device used in a medical environment or any of a number of other locations.

Figure 2:
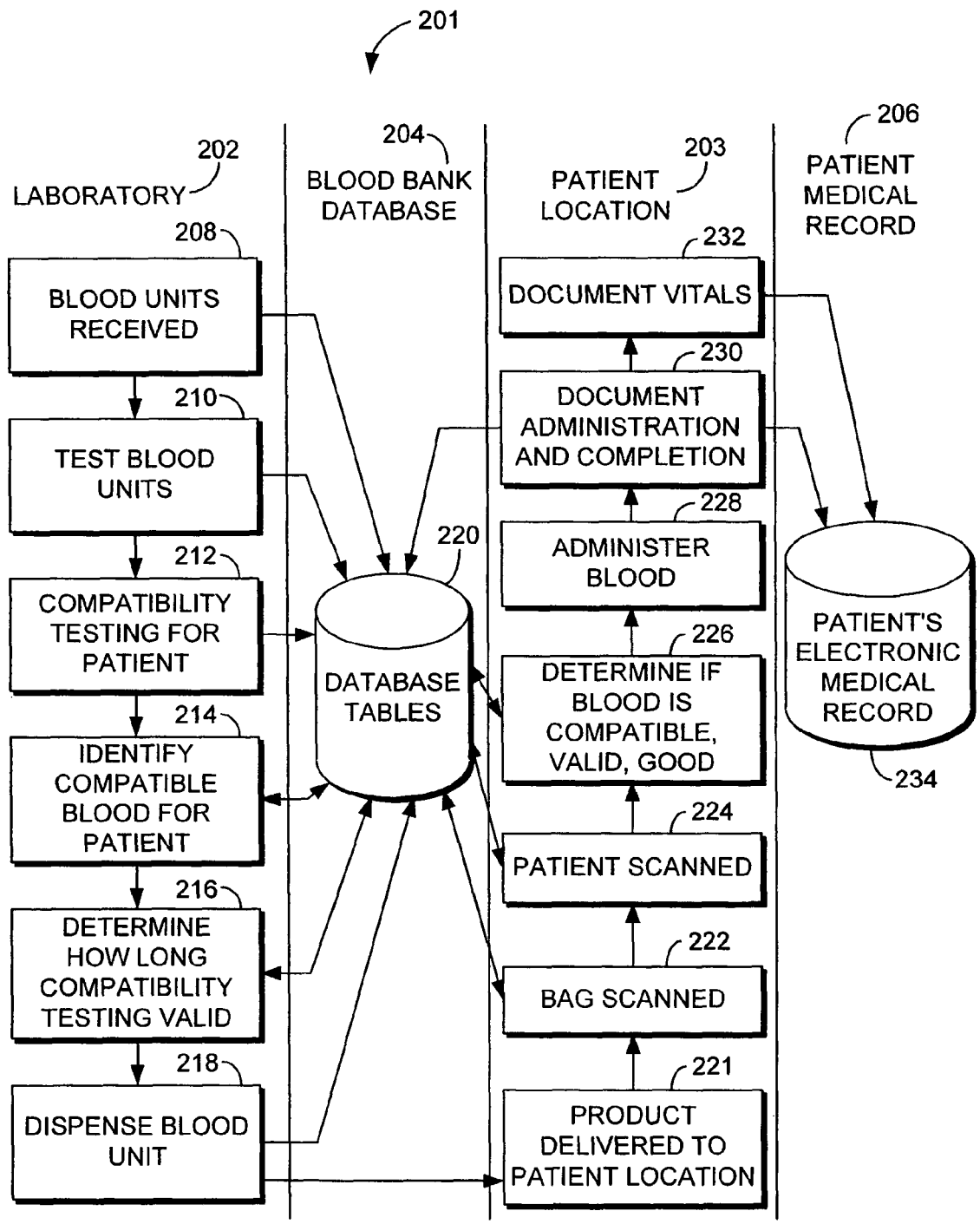
FIG. 2 is a diagram of a system and method for documenting information in the blood transfusion process in accordance with an embodiment of the present invention.

With reference to FIG. 2, a flow diagram of the overall process 201 of blood product receipt and blood product administration is shown. In the blood bank laboratory or department 202, blood product units are received and placed into the department's inventory at block 208. The blood bank laboratory may be part of a healthcare facility. The blood product units may be received from an affiliated or non-affiliated blood product supplier such as the American Red Cross, etc.

Figure 3A:
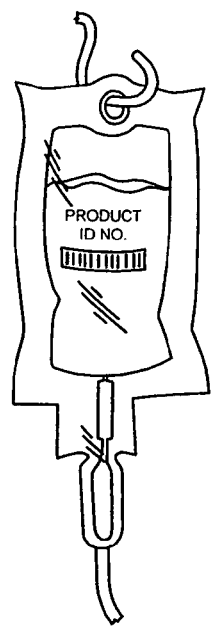
FIG. 3A is a drawing of an exemplary blood product and associated product identification number.
Figure 3B:
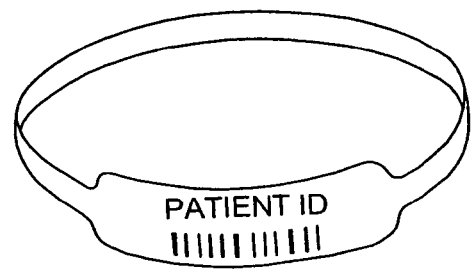
FIG. 3B is a drawing of an exemplary patient identification bracelet and associated patient identification information.
Figure 3C:
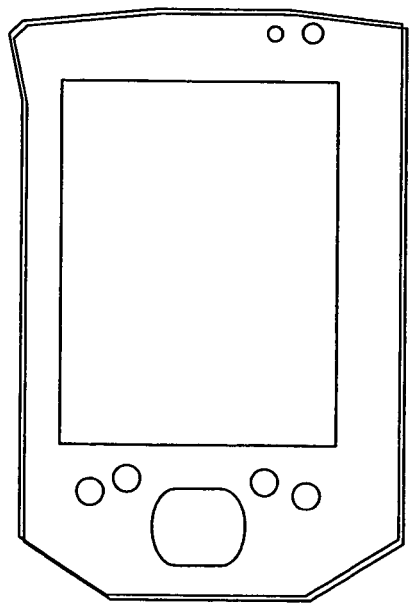
FIG. 3C is an exemplary hand held computing device for entering data in accordance with an embodiment of the present invention.

Information for each blood product unit received is documented in a database or table as shown in FIG. 4. FIG. 4 is an exemplary table from a database and the database may be any format. Information for each blood product unit received is entered in database 220. Database 220 may reside in the blood bank laboratory 202 or may be available to the blood bank laboratory via a network. The information documented includes but is not limited to, the product identification number, the type of blood product (whole blood, packed red blood cells, platelets and plasma), the blood product ABORh group and type, the blood product expiration date and any known red cell antigens. The blood product unit is identified by unit number or other identification value as shown in FIG. 3A. Preferably, the blood product unit number is the number or identifier given to the blood unit at the time it is collected from the donor. For example, the identifier is the blood unit number assigned by the blood product supplier. A common number or identifier is remains the same for the blood product unit. The patient is identified by a medical record number, financial number, or other identification record code or entry as shown in FIG. 3B. Alternatively, bar-coded information on the blood product units brought into the blood bank inventory is scanned or read to insure that the product number, product type and expiration date are correctly transferred into the database 220.

At block 210 of FIG. 2, blood product confirmation testing is performed as necessary for blood product units received for inventory. For example, the blood product's labeled ABORh group and type may be confirmed by the blood bank laboratory. Results of the blood product confirmation testing are documented in a database 220 containing the exemplary table shown in FIG. 4. Once confirmed, the blood product unit is placed in inventory for use until the blood product expires or is otherwise found unacceptable for transfusion.

At block 212 of FIG. 2, blood compatibility testing for a patient is performed as necessary. Blood specimens are collected from a patient and are evaluated to determine what blood product units in inventory in the blood bank laboratory are compatible for the patient. The laboratory will determine which blood products should be evaluated for transfusion acceptability based on the patient and the organization's policies and procedures.

Patient specimens used for compatibility testing must be collected from the right patient. Bar code technology conforming to the Health Industry Bar Code (HIBC) Provider Applications Standard is used to assure a positive match between patient wristband information and bar coded patient identification information on blood specimen collection labels. When the identifiers do not match, a specimen is not recorded as having been collected. The system captures collection date/time as well as the identity of the phlebotomist. Specimen accession numbers and unique container identifiers are assigned and tracked by the system. This information may be included in bar code format on specimen labels applied at the sample at the time of collection.

Specimen sample identification numbers (displayed as a bar code or other format) applied to specimens at the time of collection may be used to retrieve orders into blood bank result entry applications, insuring that the appropriate specimen is selected for compatibility testing. The system is capable of printing product tags that include multiple bar coded patient identifiers.

With reference again to FIG. 2, at block 214, blood product units testing as compatible for possible transfusion for the patient are identified as such and products testing as incompatible for transfusion are also identified. Typically, the blood bank laboratory department retains the blood product units that have been tested for a patient within the laboratory storage areas as appropriate for the actual blood product unit and type. The units identified as compatible for transfusion are labeled and identified as such in the database 220. Additionally, in some instances, the system identifies the amount of time the compatibility testing is valid for at block 216. The compatibility test results are set to expire after a set amount of time. This time may vary based on patient and product type.

In emergency situations where the patient requires a blood product transfusion before compatibility testing can be performed, the patient may receive a transfusion using the emergency dispense guidelines. The laboratory may subsequently perform compatibility testing as indicated by the type of blood product transfused, but this may occur simultaneously or after the transfusion has occurred.

At block 218 of FIG. 2, the unit is removed from storage when a patient requires transfusion of a blood product. The blood product unit is dispensed for purposes of transfusion to the specified patient. The unit status in the database 220 is updated to denote that the product has been dispensed for the purpose of transfusion. Validation may be performed to ensure that the unit is appropriate for the patient based on the known information about the unit and the patient and the type of transfusion requested (e.g. emergency dispense or non-emergency dispense). For example, in a non-emergency dispense situation, the specific compatibility testing of the particular blood product and patient is used as described above. In an emergency dispense situation, the system may also evaluate known information about the patient from previous blood testing procedures such as known blood group, type and antibodies during the dispense assessment. Alternatively, in an emergency dispense situation, the system may determine that blood group "O" blood is valid since blood group "O" is historically viewed as universal and does not cause ABO incompatibility transfusion reactions.

Confirmation of the patient's identity and the product's identity (and appropriateness) must be completed before the actual transfusion steps may begin. In an embodiment, the transfusion steps begin at block 221 when the blood product is delivered to the patient location 203. Next, the blood product and patient are positively identified for the system. This may be achieved electronically, by scanning (or otherwise identifying) the patient at block 224 and scanning (or otherwise identifying) the blood product unit to be transfused at block 222. In an alternative embodiment, the blood product unit may be identified in the laboratory before it is delivered to the patient's bedside.

At block 226, the blood product's compatibility for the patient, as determined by laboratory compatibility testing, is determined by directly querying and accessing the database 220. The database 220 may reside anywhere such as on a network or may be downloaded to a handheld device. In the event of a need to dispense a blood product unit for emergency transfusion, blood product compatibility testing may not have been completed. In this situation, the database 220 is accessed for emergency dispense validation rules.

If the blood product unit was found to have been tested and noted in a test result in the database as compatible for the identified patient, the system notifies the user that it is safe to proceed to the next step in the transfusion process at block 228 of FIG. 2. At block 230, once the transfusion has been completed, the database 220 is notified. The patient vital signs are taken before, during and after the blood transfusion at block 232 and are documented in an electronic medical record database 234. The database 234 may include the patient's electronic medical record 206.

Figure 5A:
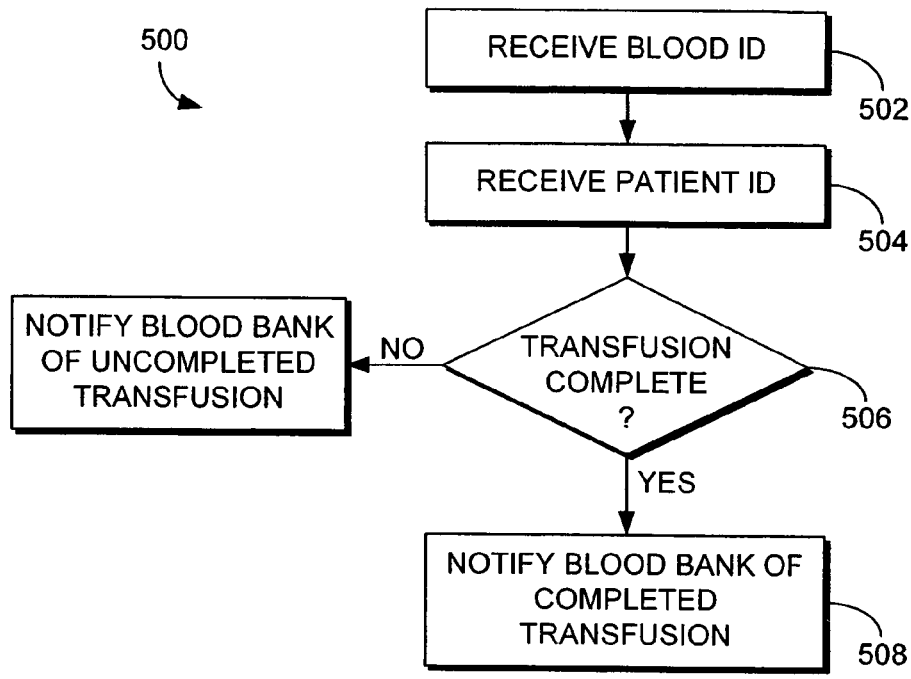
FIG. 5A is a flow diagram of a method for notifying a blood bank of a completed blood transfusion in accordance with an embodiment of the present invention.

With reference to FIG. 5A, a method 500 for notifying a blood bank laboratory of a completed or uncompleted transfusion is shown. At block 502, a blood product number or other identifier of a blood product unit is received. At block 504, a patient number or other identifier is received. At block 506 it is determined whether the transfusion of the blood has been completed. If so, at block 508, a blood bank database is notified of the completion of the transfusion. Based on the blood product number and patient identifier, the blood bank database is updated to reflect that a particular blood product unit has been dispensed to a patient. If at decision block 506 it is determined that the blood transfusion has begun but has not been completed, at block 510, the blood bank database is notified of the incomplete transfusion. Other information also may be sent to the blood bank database such as the volume of blood product transfused and time and date of beginning and completion of the transfusion. This provides the blood bank database with accurate information about actual transfusion times and status.

Figure 5B:
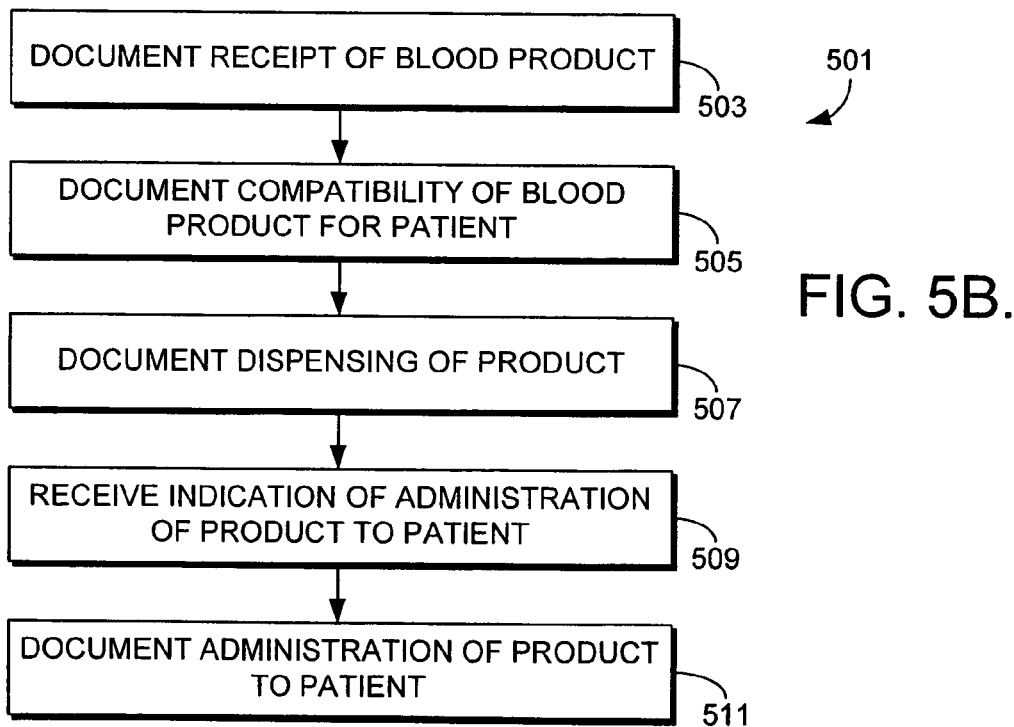
FIG. 5B is a flow diagram of a method for documenting administration of a blood product to a patient in accordance with an embodiment of the present invention.

With reference to FIG. 5B, a method 501 for documenting administration of a blood product to patient is shown. At block 503 the blood bank documents the receipt of a blood product unit. The blood product unit is identified by the product identification number given to the unit by the collection agency. Other information regarding the blood product unit is also documented included type of blood product (i.e., whole blood, packed red blood cells, platelets and plasma), blood product ABORh group and type, blood product expiration date and known red cell antigens. For example, in FIG. 4, blood product id unit 001 is identified by its product identification number "001" and the type of blood AB– is document for blood product unit 001.

Referring again to FIG. 5B, at block 505 the results of compatibility testing of the blood for a patient are documented. For example, in the exemplary database of FIG. 4, blood product unit 001 is identified as compatible for patient A but not compatible for patient B. At block 507 of FIG. 5B, it is documented in the database when the product has been dispensed for a patient. For example, in FIG. 4, it is documented that blood product unit 002 was dispensed for patient C but not for patient D. At block 509 of FIG. 5B, indication of administration of the blood product unit is received. The healthcare provider administering the blood product unit indicates that the blood product unit has been transfused to the patient and this is transmitted to the database. At block 511, the administration of the product to the patient is documented in the database. For example, in FIG. 4, the entry for blood product unit 002 to patient C is updated to reflect that the transfusion was completed.

Figure 6:
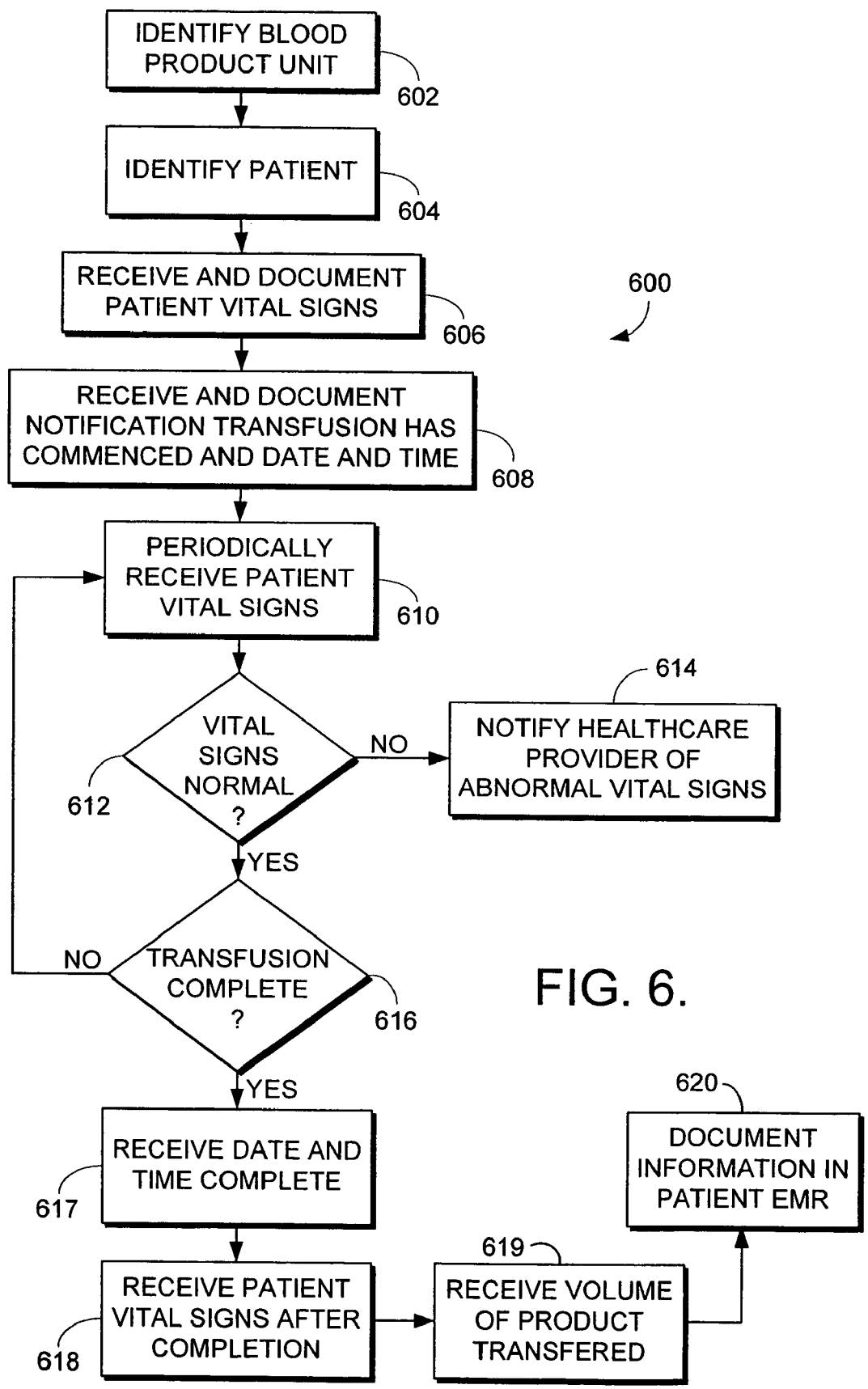
FIG. 6 is a flow diagram of a method for documenting patient vital signs before, during and after a blood transfusion in accordance with an embodiment of the present invention.

With reference to FIG. 6, a method 600 for documenting patient vital signs before, during and after a blood transfusion is shown. Following identification of the blood product unit at block 602 and patient at block 604, vital signs for the patient are received at block 606. The identification of the healthcare provider obtaining the vital signs for the patient may also be received at block 606. At block 608, notification that the transfusion has commenced and the start date and time of the transfusion are received. Additionally, data regarding the identification of the personnel initiating the transfusion may also be received at block 608.

Periodically after the transfusion has commenced, patient vital signs are received at block 610. Patient vital signs may include, bat are not limited to, heart rate, blood pressure, temperature, etc. As vital signs are received at block 610, it is determined whether the vital signs for the patient are within a normal range at decision block 612. If the vital signs received for the patient at block 610 are not considered to be within a normal range, the healthcare provider administering the transfusion is notified of the abnormal vital signs at block 614.

If at decision block 612 the vital signs received for the patient are within a normal range, at block 616 it is determined whether the transfusion is complete. If not, the system will continue at blocks 610-616 until the transfusion is complete. If at decision block 616, it is determined that the transfusion is complete, at block 617 the system receives the date and time of when the transfusion is complete. The identification of the personnel completing the transfusion may also be received at block 617.

At block 618, after the completion of the transfusion, the system receives patient vital signs. At block 619, the volume of the blood product unit that has been transferred to the patient is received. At block 620, the data regarding the transfusion, date of start and stop times and vital signs are documented for the patient. In an integrated unified medical computing environment, this data may be documented in the patient's electronic medical record. The data may be documented at any time during the method described in FIG. 6. Any of the above data such as vital signs, care and time information, may be received by entry of user into an integrated healthcare environment using a remote computer. Furthermore, the information may also be received directly from a healthcare device or instrument.

Figure 7:
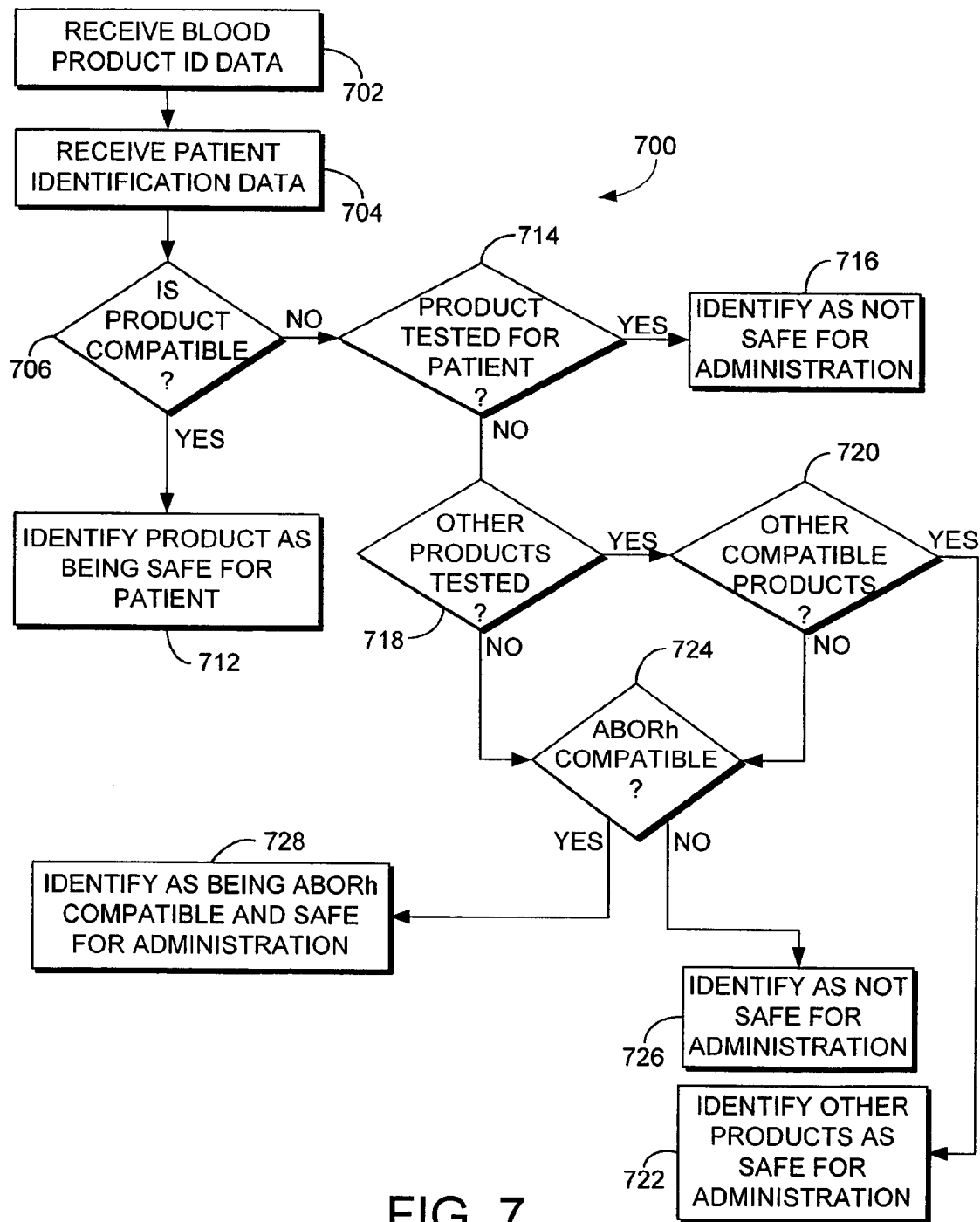
FIG. 7 is a flow diagram of a method for ensuring that a blood product is compatible for a particular patient in accordance with an embodiment of the present invention.

With reference to FIG. 7, a method 700 for determining whether a blood product unit to be administered to a patient has been tested for compatibility. At block 702, blood product identification data is received. This may be by scanning or otherwise identifying the blood product unit to be transfused. For instance, the blood product unit may be identified by a unit number or other identification value as shown in FIG. 3A.

At block 704, patient identification data is received. The patient may be identified by a medical number, financial number or other identifier. In FIG. 3B the identifier is shown on a patient identification bracelet capable of being scanned in an embodiment of the invention. At decision block 706 it is determined whether the product identified at block 702 has been tested for and is compatible for the patient identified at block 704. This is done by accessing a blood bank database via a network or from data stored on a remote handheld or other type of computer. The data includes results from compatibility testing completed and stored previously for the patient. An exemplary database/table of compatibility data and other data for blood product units is shown in FIG. 4. For example, compatible blood products for patient A includes blood unit product 001 and 003. Compatible blood for patient C includes unit 002 but not unit 003. Determining compatibility may also include determining whether the compatibility testing performed by the blood bank laboratory has expired. For example, compatibility testing for blood product units 001, 002 and 003 is only good for 72 hours. For example, the system may perform additional checks, including confirmation that the blood product has been dispensed by the transfusion service within a site-defined acceptable time frame. For example in FIG. 4, blood product units 001 and 002 must be transfused by 1:30 a.m. on May 11, 2005. If at decision block 706 it is determined that the product has been tested and is compatible for the patient, at block 712 the product is identified as being compatible and safe to administer. For example, a message may be sent to the healthcare provider to administer the blood unit product.

If at block 706, after accessing the blood bank database containing compatibility testing results it is determined that the product has not been identified as compatible by the testing laboratory, then at decision block 714 it is determined whether the blood product unit identified at block 702 has been tested for compatibility for the patient. If at decision block 714 it is determined that the product has been tested for the patient, the blood product unit is identified as not compatible and unsafe for administration at block 716. The healthcare provider administering the blood unit is notified that the blood unit is not compatible for the identified patient and should not be transfused. If at decision block 714, the blood product unit is found to have not been tested for the patient, at block 718 it is determined whether any other blood product units had been previously tested for compatibility with the patient and are still available for transfusion purposes. If at decision block 718 it is determined that no other blood product units have been tested for compatibility with the patient, the system proceeds to decision block 724.

If at decision block 718 it is determined that another blood product unit has been tested and is available for transfusion to the patient, it is determined whether the other tested blood product units have been tested for compatibility for the patient at block 720. If at decision block 720 it is determined that other blood product units have tested as compatible for the patient, at block 722, the compatible blood product units are identified. This may be accomplished by sending a message to the healthcare provider administering the blood transfusion of the other unit's availability and notifying the blood bank of the new blood product unit needed. It at decision block 720 it is determined that other blood product units have not tested as compatible for the patient the system proceeds to decision block 724.

At decision block 724, the system determines whether the blood product unit identified at block 704 is ABORh compatible for the patient. In other words, the system determines based on the patient's blood group type and the blood group and type of the blood product unit if the blood product unit can be safely administered to the patient. This option allows an emergency override of the requirement that compatibility testing for the patient be performed. For example, with reference to FIG. 4, patient E needs an emergency blood transfusion. Compatibility tests have not been performed for patient E. However, it is known that patient E has O+ blood type. By accessing the blood bank database it would be determined that the blood product unit 002 provided is O+ and is compatible for patient E's O+ blood type and it is safe to administer the blood product unit. Other emergency dispense criteria such as those described above may be employed in embodiments of this invention. In other embodiments, when compatibility is not present between the identified blood product and patient, guidelines for determining the least incompatible blood product for the patient may be employed in accordance with this invention.

If the patient's blood type (as determined by the laboratory's testing) and the unit's ABORh blood type (as determined by the suppliers label and the laboratory's confirmation testing) are incompatible for transfusion at block 724, the healthcare provider administering the blood product unit is notified of the incompatibility at block 722 and that the transfusion of the identified unit should not occur because of possible harm to the patient.

The present invention has been described in relation to particular embodiments, which are intended in all respects to be illustrative rather than restrictive. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations, and are contemplated within the scope of the claims. Not all blocks listed in the various figures need to be carried out in the specific order described.

The invention claimed is:

1. One or more computer-storage media having computer-executable instructions for performing a method for processing patient vital signs during blood product administration in a computerized healthcare environment, the method comprising:

identifying a blood product to be administered to a patient by receiving, at a remote computer at the patient's bedside, a blood product identifier identifying the blood product to be administered to the patient;

identifying the patient by receiving, at the remote computer at the patient's bedside, a patient identifier identifying the patient;

communicating the blood product identifier and the patient identifier to a blood bank database to maintain a record of the blood product administration;

communicating a start time of the blood product administration to the blood bank database;

receiving vital signs, at the remote computer at the patient's beside, at a first time instance for the patient identified at the patient's bedside during administration of the blood product identified at the patient's bedside by a healthcare provider;

determining whether the vital signs at the first time instance for the patient during the blood product administration are within an acceptable range by comparing the vital signs received at the remote computer at the patient's beside with an acceptable range of vital signs during blood product administration;

upon determining that the vital signs at the first time instance for the patient during the blood product administration are within the acceptable range, determining whether the blood product administration is complete;

upon determining that the blood product administration is not complete, notifying the blood bank database that the blood product administration is not complete such that the blood bank database includes accurate information regarding blood product administration status and receiving, at the remote computer at the patient's beside, vital signs at a second time instance for the patient during the blood product administration;

determining whether the vital signs at the second time instance for the patient obtained during the blood product administration are within the acceptable range by comparing the vital signs at the second time instance received from the remote computer at the patient's beside with the acceptable range of vital signs during blood product administration;

upon a determination that the vital signs at the second time instance are not within the acceptable range, displaying a notification at the bedside of the patient to the healthcare provider currently administering the blood product to the patient; and automatically, without user intervention, documenting in a patient database the vital signs for the patient and whether the vital signs for the patient are within the acceptable range.

2. The media of claim 1, wherein the patient database is the patient's electronic medical record.

3. The media of claim 1, further comprising:
receiving and documenting identification of a healthcare provider taking the patient vital signs.

4. The media of claim 1, further comprising:
receiving and documenting identification of a healthcare provider administering the blood product.

5. The media of claim 1, further comprising:
receiving and documenting patient vital signs before blood product administration.

6. The media of claim 5, further comprising:
receiving and documenting identification of the healthcare provider taking the patient vital signs before the blood product administration.

7. The media of claim 1, further comprising:
receiving the time and date when the patient vital signs were taken.

8. The media of claim 1, further comprising:
receiving and documenting the identification of the healthcare provider completing the blood product administration.

9. The media of claim 1, wherein the patient vital signs are input using a remote computing device.

10. The media of claim 1, wherein the patient vital signs are received directly from a healthcare device.

11. The media of claim 1, wherein the patient is identified by a patient identification number.

12. The media of claim 11, wherein the patient identification number is received by scanning a bar code on a patient identification bracelet.

13. The media of claim 1, wherein the blood product is identified by a blood product identification number assigned by the blood product supplier.

14. A computing device for processing patient vital signs during blood product administration, the computing device comprising:

a first identifying component for identifying a blood product to be administered to a patient;

a second identifying component for identifying the patient;

a first communicating component for communicating an identifier identifying the identified blood product to be administered to the patient, a patient identifier identifying the patient, and a start time of a blood product administration of the identified blood product to the identified patient;

a receiving component for receiving vital signs for the patient during the blood product administration by a healthcare provider;

a first determining component for determining whether the vital signs for the patient obtained during the blood product administration are within an acceptable range;

a second determining component for determining whether the blood product administration is complete based upon a determination that vital signs for the patient obtained during the blood product administration are within the acceptable range;

a second communicating component for communicating an indication that the blood product administration is not complete to the blood bank database;

a displaying component for notifying the healthcare provider currently administering the blood product that the vital signs for the patient are not within an acceptable range; and a documenting component for automatically, without user intervention, documenting in a database the vital signs for the patient and whether the vital signs for the patient are within the acceptable range.

15. The computing device of claim 14, wherein the database is the patient's electronic medical record.

16. The computing device of claim 14, wherein the receiving component receives the patient vital signs for the patient from a remote computing device.

17. The computing device of claim 14, wherein the receiving component receives the patient vital signs directly from a healthcare device.

18. The computing device of claim 14, wherein the second identifying component identifies the patient by a patient identification number.

19. The computing device of claim 14, wherein the first identifying component identifies the blood product by a blood product identification number assigned by the blood product supplier.

* * * * *